United States Patent [19]
Nicholson et al.

[11] Patent Number: 5,221,271
[45] Date of Patent: Jun. 22, 1993

[54] SAMPLE SITE WITH FLOW DIRECTORS

[75] Inventors: Warren B. Nicholson, Worthington; Glenn D. Brunner, Dublin, both of Ohio

[73] Assignee: Medex, Inc., Dublin, Ohio

[21] Appl. No.: 746,239

[22] Filed: Aug. 15, 1991

[51] Int. Cl.⁵ .............................................. A61M 25/00
[52] U.S. Cl. ..................................... 604/283; 604/905
[58] Field of Search .............. 604/283, 905, 240–243, 604/80, 83, 140–141, 256, 257; 137/896, 808, 809, 811

[56] References Cited

U.S. PATENT DOCUMENTS

| | | | |
|---|---|---|---|
| 4,390,346 | 6/1983 | Cramer et al. | 137/896 |
| 4,647,212 | 3/1987 | Hankison | 137/896 |
| 4,838,858 | 6/1989 | Wortham et al. | 604/257 |
| 4,846,794 | 7/1989 | Hertzer | 604/257 |
| 4,935,009 | 6/1990 | Caldwell et al. | 604/83 |
| 4,967,797 | 11/1990 | Manska | 604/83 |

OTHER PUBLICATIONS

Baxter Vamp Brochure 170000-2 Rev. A (6 pp.) (1989).
Baxter Vamp Brochure 106865-2, Rev. A. (4 pp.) (1989).

Primary Examiner—C. Fred Rosenbaum
Assistant Examiner—M. Mendez
Attorney, Agent, or Firm—Wood, Herron & Evans

[57] ABSTRACT

A sample site for obtaining a whole blood sample includes flow directors in the ports. The flow directors may include ramp surfaces. Blood flowing into the sample site is diverted by the flow directors to mix with and flush out all of the saline otherwise present in the sample site to allow for a whole blood sample to be taken.

20 Claims, 2 Drawing Sheets

SAMPLE SITE WITH FLOW DIRECTORS

BACKGROUND OF THE INVENTION

I. Field of the Invention

The present invention relates to sample sites to be coupled via a catheter or the like to a patient's circulatory system and through which a sample of the patient's blood may be withdrawn.

II. Description of the Prior Art

Sample sites typically include a fluid cavity in line with tubing connected to a patient's circulatory system. Blood may be withdrawn through the sample site by inserting a needle into the fluid cavity through a latex plug in the sample site and withdrawing the fluid in the cavity.

An exemplary system which may advantageously employ a sample site for withdrawing blood is a blood pressure monitoring system in which a catheter inserted into a patient's blood vessel is connected via tubing to a blood pressure sensor, and a stopcock, which either connects the tubing to a supply of saline solution or a reservoir. A sample site may be included in-line with the tubing midstream between the patient and the stopcock to facilitate blood sampling without an additional needle puncture to the patient.

When the tubing is connected through the stopcock to the saline source, the sensor is in fluid communication with the patient's circulatory system to sense the patient's blood pressure. When it is desired to take a sample of the patient's blood, rather than puncturing the patient with another needle, the sample site may be used. To this end, the stopcock is turned to disconnect the saline source from the patient's circulatory system and instead couple the patient's circulatory system to the reservoir. Saline will flow away from the patient and into the reservoir as the patient's blood flows through the tubing and into and through the sample site. Thereafter the needle of a syringe is inserted into the sample site and blood is withdrawn therefrom with the syringe. The needle is then removed from the sample site after which the stopcock is turned to disconnect the patient's circulatory system from the reservoir, reestablishing the connection between the patient's circulatory system and the saline source so as to reestablish the blood pressure monitoring function.

When using a sample site as in the above-described system, it is desirable that whole blood be removed from the patient through the sample site. That is, it is desirable that the blood removed through the sample site not be mixed with any other fluid, such as the saline solution normally present in the sample site during blood pressure monitoring. However, with previously existing sample sites, not all of the saline may be displaced from the cavity during a sampling operation leading to diluted blood samples rather than whole blood samples as is desired.

SUMMARY OF THE INVENTION

The present invention provides a sample site which minimizes or eliminates the likelihood that saline will remain in the sample site to dilute the blood sample.

As will be appreciated, a typical sample site includes a pair of tubular ports disposed on opposite sides of the fluid cavity and aligned such that fluid may flow directly therebetween along a common axis. The inner cylindrical walls of the ports define circular openings into the cavity, also along the common axis. To the extent fluid flow into and through the cavity is directly between the ports i.e., along the common axis, the flow will likely be a laminar flow. As a result of the laminar flow, some of the saline solution above, below and around the laminar flow path may not be flushed from the cavity by the blood flowing therethrough. The remaining saline solution may thus dilute the blood sample when the sample is withdrawn from the cavity.

To this end, and in accordance with the principles of the present invention, the sample site is modified to include flow directors adjacent the fluid cavity. The flow directors create a flow of fluid throughout the sample site cavity which flushes the saline solution out, leaving only whole blood in the sample site cavity for blood sampling. More particularly, a flow director is preferably molded into one or both of the sample site ports and provides a ramp surface within the port by which to divert the flowing fluid away from the direct line between the ports or the common axis. The resulting non-laminar or swirling flow tends to flush all of the saline out of the cavity so as to allow whole blood samples to be drawn.

Preferably, the flow directors are bidirectional so that the sample site may be inserted in-line without regard to which port is on the patient or saline side of the system. The bidirectional nature of the flow directors also provides reverse flushing action. Thus, when the pressure monitoring system is to be reestablished after a blood sample is taken, all of the remaining blood will be flushed back into the patient's circulatory system. The flow directors are made bidirectional by, for example, molding flow directors into both ports with the ramp surfaces oppositely disposed (e.g., rotated 180° relative each other) to cause the fluid to flow in opposite directions relative the common axis, depending upon whether the fluid is flowing into the cavity from one port or the other.

These and other objects and advantages of the present invention shall become more apparent from a detailed description of the invention.

BRIEF DESCRIPTION OF THE DRAWINGS

In the accompanying drawings, which are incorporated in and constitute a part of this specification, embodiments of the invention are illustrated, which, together with a general description of the invention given above, and the detailed description given below, serve to explain the principles of the invention.

Figure 1:
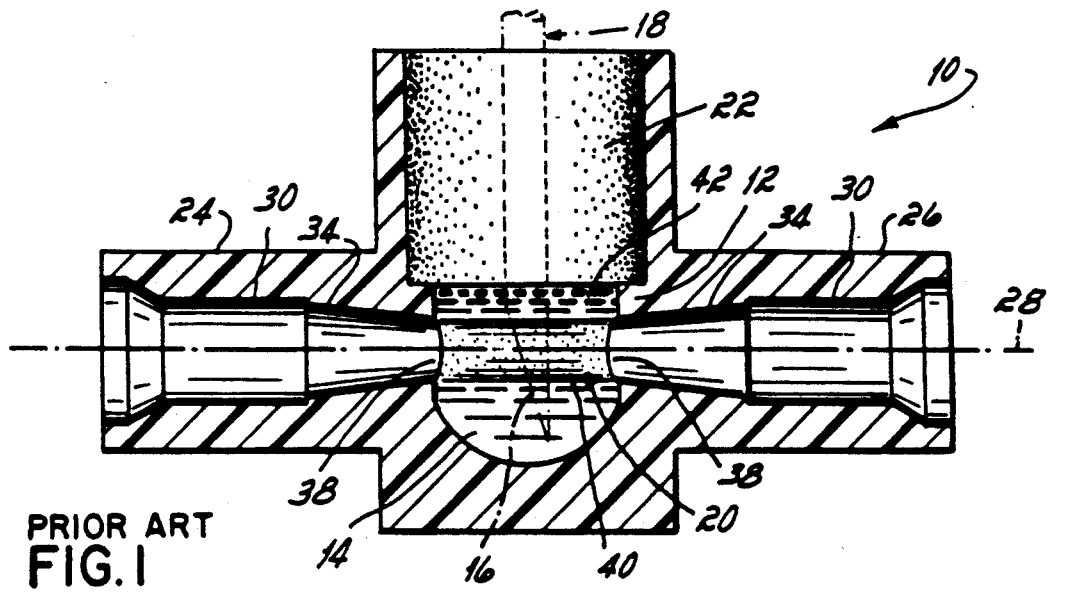
FIG. 1 is a cross-sectional view of a prior art sample site.

Flow directors 50, 52 are preferably oppositely disposed, i.e., ramp surfaces 68 and 70 are rotated 180° from each other on opposite sides of common axis 28 to render sample site 60 bidirectional. With sample site 60, it is believed that fluid 20 will flow into cavity 14 along a ramp surface (such as ramp surface 68 or 70 depending upon the direction of flow) so as to be diverted from common axis 28 and either towards Faultless 5218 pure gum latex seal 22 at the top end of cavity 14 or towards bottom end 72 of cavity 14. The continued flow of fluid 20 into one port is believed to cause fluid 20 to move towards the opposite end (top to bottom or bottom to top) of cavity 14 and swirl about until it exits the opposite port thereby flushing out the other fluid 42 (see FIG. 1) which might otherwise remain in cavity 14.

Figure 3:
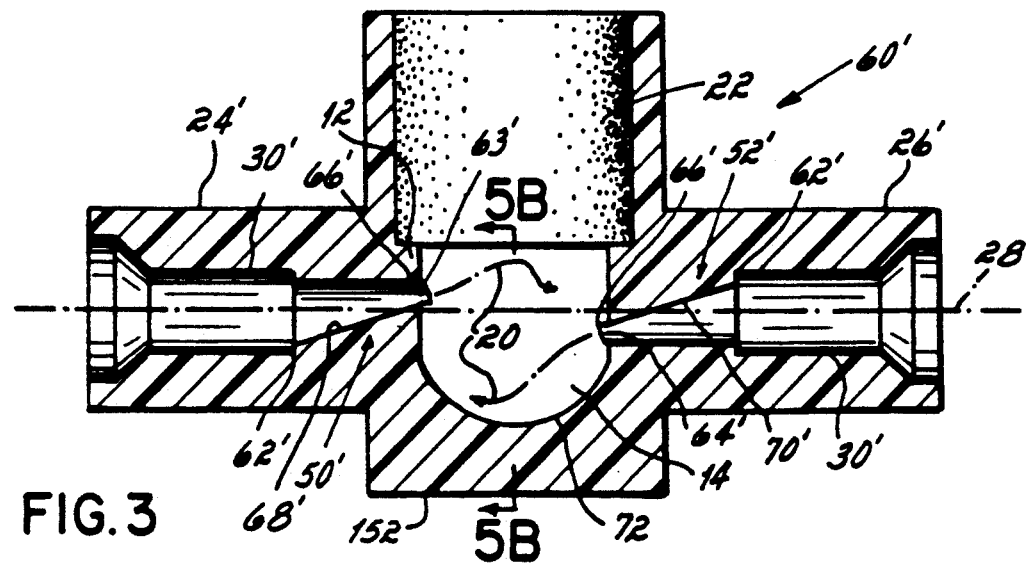
FIG. 3 is a cross-sectional view of a second embodiment of a sample site constructed in accordance with the principles of the present invention.
Figure 5A:
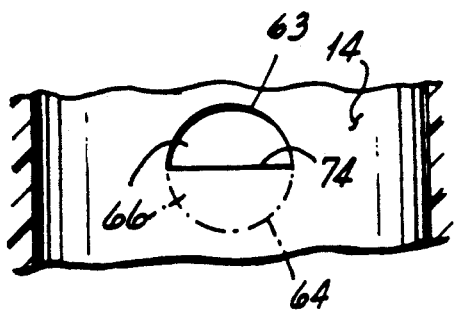
Figure 5B:
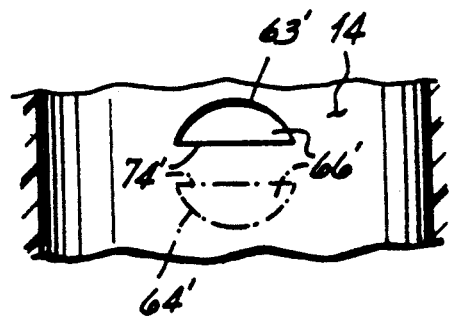

Sample site 60 is designed for use with adult patients (not shown). To this end, in polycarbonate housing 12, the diameter of cavity 14 between ports 24, 26 is about 0.220 inch with a hemispherical bottom end surface 72 having a radius of about 0.118 inch; the diameter of the cylindrical portion of ports 24, 26 is about 0.123 inch with a slight draft, and the cross-section changes from circular with a diameter of about 0.109 inch at base FIG. 5A is a cross-sectional view taken on line 5A—5A of FIG. 2;

FIG. 5B is a cross-sectional view taken on line 5B—5B of FIG. 3; and

Figure 2:
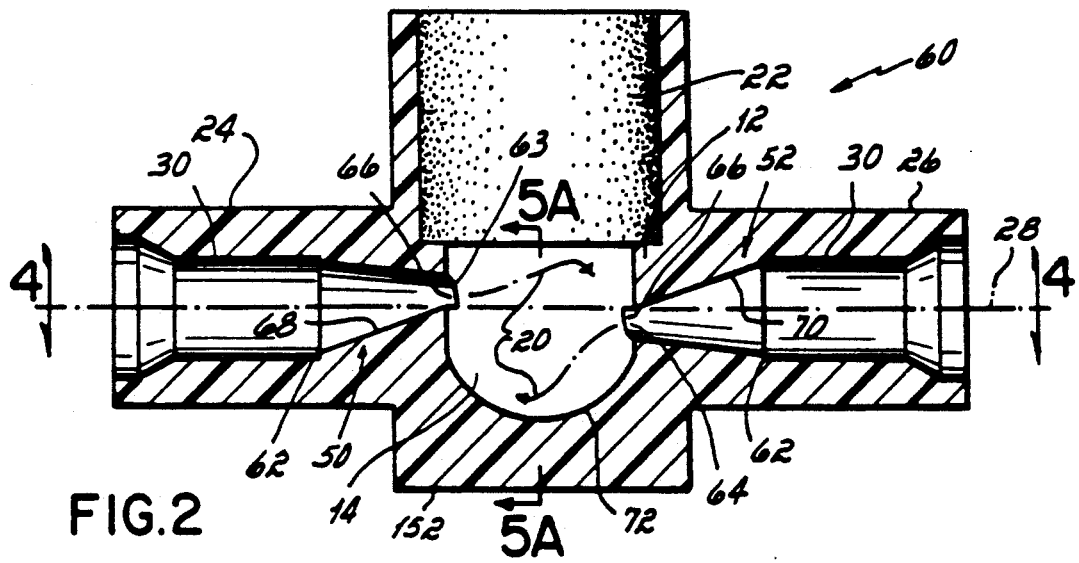
FIG. 2A is a cross-sectional view of a first embodiment of a sample site constructed in accordance with the principles of the present invention.
Figure 6:
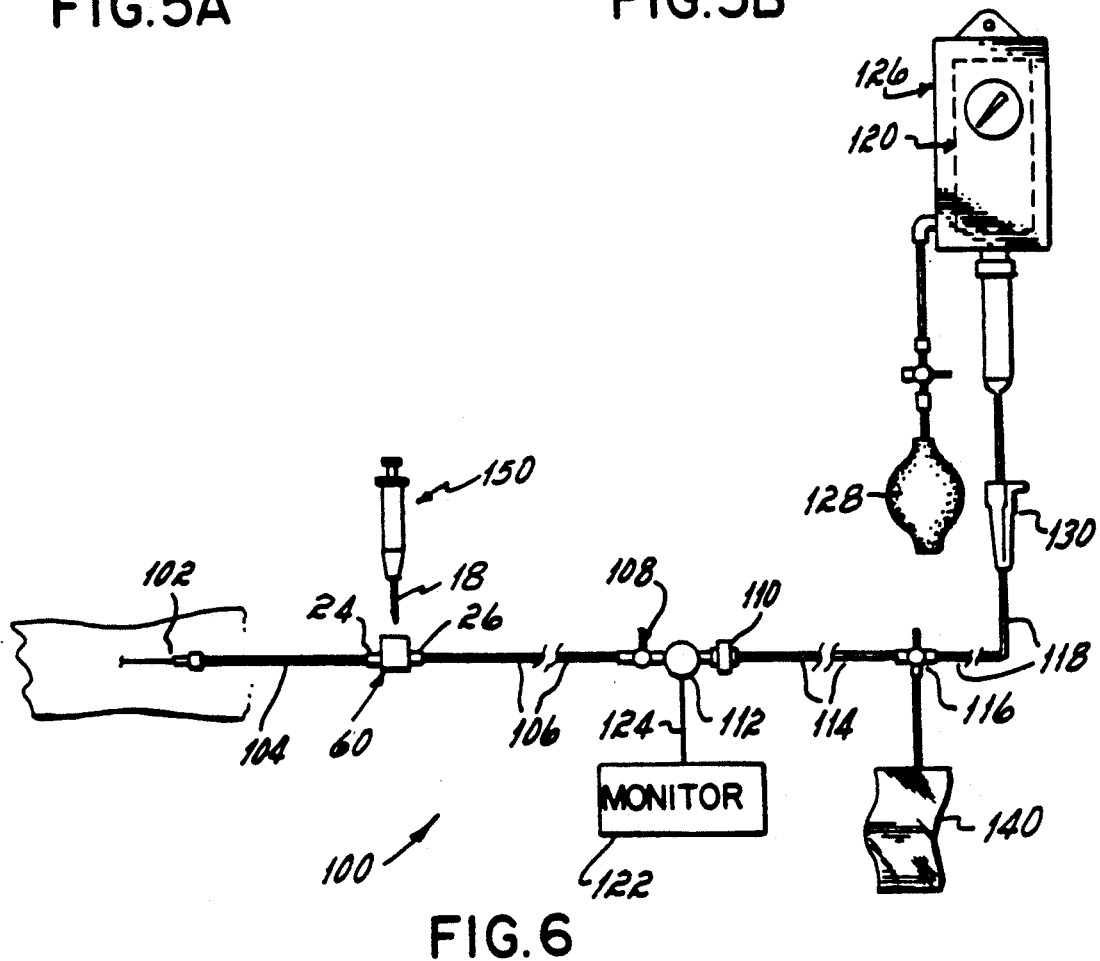

FIG. 6 is a diagrammatic view of an exemplary, closed pressure monitor/blood sampling system incorporating the sample site of FIG. 2 for purposes of explaining the principles of operation of the present invention.

DETAILED DESCRIPTION OF THE DRAWINGS

Before describing the details of the present invention, a description of a prior art sample site may be helpful in understanding the advantages of the present invention. Reference is had, therefore, to FIG. 1 in which is shown a prior art sample site 10 having a housing 12 defining a fluid cavity 14 therein sized to receive the open kerf 16 of a needle 18 therein for withdrawing from cavity 14 the fluid (such as blood 20) therein. As is well known, a seal 22 is included in housing 12 to seal cavity 14 and to allow access by penetration of the needle 18. A pair of tubular or cylindrical ports 24, 26 are connected to opposite sides of housing 12 along common axis 28. The interior walls 30 of ports 24, 26 may taper as at 34 to provide smaller diameter circular openings or inlets 38 to cavity 14 along common axis 28. When fluid such as blood 20 flows into and through cavity 14 between ports 24 and 26, fluid is believed to flow directly between inlets 38 such as along or concentric with common axis 28 to define a laminar flow path 40. As a consequence, other fluid, such as saline 42, above, below or around the laminar flow path, may remain in cavity 14 rather than be flushed therefrom by the flowing fluid 20. The result, when a blood sample is to be taken through needle 18, the sample may be a diluted blood sample.

Figure 4:
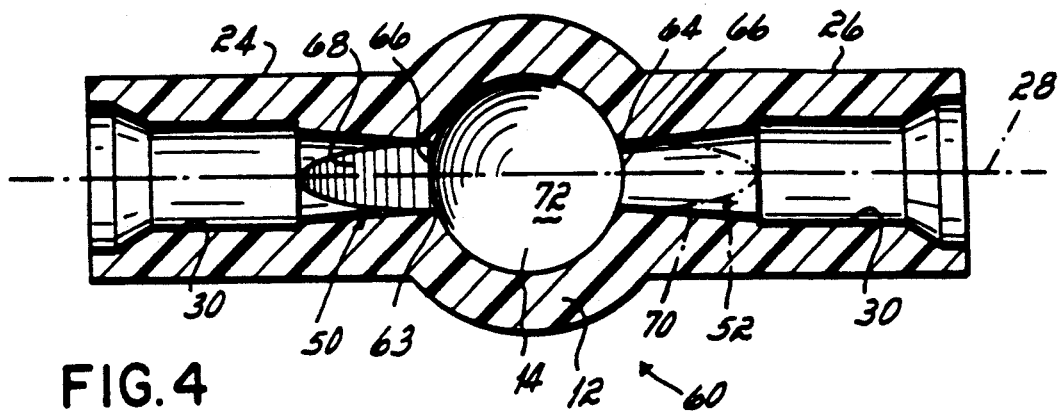
FIG. 4 is a cross-sectional view taken on line 4—4 of FIG. 2; directors 50, 52 such as exemplified by flat ramp surfaces 68, 70, respectively.

To overcome the above risk of obtaining diluted blood samples, and in accordance with the principles of the present invention, flow directors 50, 52 are preferably molded into ports 24, 26 adjacent cavity 14 such as may be seen in FIGS. 2, 4, and 5A which depict a first embodiment of a sample site 60 constructed in accordance with the principles of the present invention. As may there be seen, sample site 60 differs from sample site 10 by the inclusion of flow directors 50, 52 each of which is formed integral the interior wall 30 of ports 24, 26 such that the cross-section of ports 24, 26 changes from circular at the base 62 of flow directors 50, 52 to semicircular at the top 63 and bottom 64, respectively, of directors 50, 52 at the inlets 66 adjacent cavity 14. Preferably, the change in cross-section is continuous or smooth by providing an inclined surface to flow 62 of flow directors 50, 52 to semicircular at inlets 66 with a radius of about 0.038 inch with ramp surfaces 68, 70 defined along an angle of about 19° 58' relative a horizontal plane transverse cavity 14 and intersecting chord or base wall 74 of the associated semicircular inlet 66. It should be noted that base wall 74 of both semicircular inlets 66 are parallel and intersect common axis 28 so that when viewed end to end, inlets 66 align to define a circle as seen in FIG. 5A.

When it is desired to use a sample site for obtaining a blood sample from a neonate, a sample site similar to sample site 60 may be utilized wherein the difference is with regard to the size of the ports. To this end, and as shown in FIG. 3, neonate sample site 60' differs from adult sample site 60 in that the inner diameter of the cylindrical portions of ports 24', 26' is about 0.105 inch with a slight draft, and the cross-section changes from circular with a diameter of about 0.075 inch at base 62' of flow directors 50', 52' to semicircular at inlets 66' with a radius of about 0.035 inch, and with ramp surfaces 68', 70' defined along an angle of 18° 4' 22" relative the horizontal plane transverse cavity 14 and intersecting base wall 74' of the associated semicircular inlet 66'. In contrast to sample site 60, the base walls 74' of inlets 66', when viewed end to end, are not along common axis 28 but instead are spaced therefrom as seen in FIG. 5B.

Sample sites constructed in accordance with the present invention, such as sample site 60, may be utilized for blood sampling as will now be described with reference to the exemplary closed blood pressure monitoring/blood sampling system 100 shown in FIG. 6. System 100 may be as described in copending application Ser. No. 07/557,153 in the name of Phillip D. Messinger, entitled "Method and Apparatus for Sampling Blood", and which is assigned to the assignee hereof. The disclosure of application Ser. No. 07/557,153 is fully incorporated herein by reference. As seen in FIG. 6, catherer 102 inserted into a patient's blood vessel is connected by tubing 104 to port 24 of sample site 60. The other port 26 of sample site 60 is connected via tubing 106 to stopcock 108 and flush valve 110. Intermediate stopcock 108 and flush valve 110 is a pressure sensor 112. Flush valve 110 is connected via tubing 114 to stopcock 116 and thence via tubing 118 to a source 120 of saline. As a consequence, when stopcocks 108 and 116 are properly positioned, sample site 60 is in-line between saline source 120 and catheter 102 so that saline may flow therethrough and allow blood pressure monitoring by blood pressure sensor 112. Sensor 112 is coupled to blood pressure monitor 122 via sensor lead 124 as is well understood. As is also well known, saline source 120 may be pressurized by pressure infuser 126 and its associated squeeze bulb 128 and may also be flow controlled through roller clamp 130.

In use, when it is desired to obtain a blood sample, stopcock 116 is operated to connect catheter 102 to reservoir 140 through stopcock 116 which also disconnects catheter 102 from saline source 120. Blood from the patient will then flow out of catheter 102 and towards reservoir 140 pushing saline ahead of the blood. As the blood flows into and through cavity 14 of sample site 60, it will flow along ramp surface 68 and away from common axis 28. The flow thus set up inside cavity 14 mixes with and flushes out the saline 42 otherwise normally in cavity 14 until only whole blood remains, undiluted by saline. Stopcock 108 may then be manipulated to stop further flow of fluid and a whole blood sample taken by inserting needle 18 through latex plug 22 and into cavity 14 and withdrawing the blood sample by manipulation of syringe 150 as is well known.

After the sample is taken and needle 18 withdrawn, stopcocks 108 and 116 may be manipulated to restore the catheter-to-saline source connection causing blood remaining in system 100 downstream of stopcock 116 to be driven back into the patient. Blood mass loss is minimized further by the reverse flow of saline into sample site 60 through port 26 with a flushing action on the blood similar to the saline flush action above described.

Although not shown, sample sites 60, 60' may be provided with support structure formed integral or attached to the bottom exterior 152 thereof. Such support structure may be a transverse plate by which to tape or strap the sample site to the patient or may be a perpendicular plate by which a clinician may grasp the sample site.

While the present invention has been illustrated by the description of embodiments thereof, and while the embodiments have been described in considerable detail, it is not the intention of applicants to restrict or in any way limit the scope of the appended claims to such detail. Additional advantages and modifications will readily appear to those skilled in the art. For example, the flow directors need not be ramps but could be offset tapers which cause the inner walls of the ports to taper, still to circular cross-section openings, but offset from the common axis as in the case of the semicircular openings to thereby divert fluid flow from the common axis and provide a desirable non-laminar flow within cavity 14. The invention in its broader aspects is therefore not limited to the specific details, representative apparatus and method, and illustrative examples shown and described. Accordingly, departures may be made from such details without departing from the spirit or scope of applicants' general inventive concept.

What is claimed is:

1. A sample site comprising:
   a housing having a cavity therein;
   seal means for selectively accessing fluid in the cavity;
   A pair of ports connected to the housing and in fluid communication with the cavity; and
   flow director means in the ports for creating non-laminar flow of fluid in the cavity from one of the ports to the other port.

2. The sample site of claim 1, the ports being oppositely disposed along a common axis.

3. The sample site of claim 1, the flow director means including a ramp in at least one of the ports adjacent the cavity.

4. The sample site of claim 1, the flow director means including a ramp in each of the ports adjacent the cavity.

5. The sample site of claim 4, the ramps being rotated 180° relative each other.

6. The sample site of claim 1, the flow director means being positioned in the ports such that they are rotated 180° relative each other.

7. A sample site comprising:
   a housing having a cavity therein;
   seal means for selectively accessing fluid in the cavity;
   a pair of ports connected to opposite sides of the housing, the ports being in fluid communication with the cavity through an inlet in each of the ports; and
   a first flow director within a first of the ports whereby to diver fluid entering the cavity through the port from flowing along a direct line from the inlet of one of the ports to the inlet of the other port 8. The sample site of claim 7, the first flow director including a ramp surface extending away from the interior wall of the first port and towards the cavity.

9. The sample site of claim 8 wherein the ramp surface extends to the cavity so as to define a semicircular cross-section to the inlet of the first port.

10. The sample site of claim 8 wherein the ramp surface is flat.

11. The sample site of claim 7 further comprising:
    a second flow director within a second of the ports whereby to divert fluid entering the cavity through that port from flowing along a direct line between the inlets.

12. The sample site of claim 11, the flow directors each including a ramp surface extending away from the interior wall of the associated port and towards the cavity.

13. A sample site comprising:
    a housing having a cavity therein;
    seal means for selectively accessing fluid in the cavity;
    a pair of ports connected to opposite sides of the housing along a common axis, the ports being in fluid communication with the cavity through inlets in the ports; and
    a first ramp surface within a first of the ports adjacent the inlet thereof to produce a flow from one of the ports to the other port.

14. The sample site of claim 13, the ramp surface being connected to the interior wall of the first port at a location spaced from the inlet thereof.

15. The sample site of claim 14 wherein the ramp surface extends to the cavity so as to define a semicircular cross-section to the inlet of the first port.

16. The sample site of claim 13 further comprising a second ramp surface within a second of the ports adjacent the inlet thereof.

17. The sample site of claim 16, each ramp surface being connected to the interior wall of the associated port at a location spaced from the inlet thereof.

18. The sample site of claim 16 wherein each ramp surface extends to the cavity so as to define a semicircular cross-section to the inlet of the associated port.

19. The sample site of claim 16, each of the ramp surfaces being aimed in a different direction.

20. The sample site of claim 16, the ramp surfaces being rotated 180° relative each other.

* * * * *

UNITED STATES PATENT AND TRADEMARK OFFICE
CERTIFICATE OF CORRECTION

PATENT NO. : 5,221,271

DATED : June 22, 1993

INVENTOR(S) : Warren B. Nicholson et al

It is certified that error appears in the above-indentified patent and that said Letters Patent is hereby corrected as shown below:

Column 2, line 59, delete "directors 50, 52, such as exemplified by flat ramp"

Column 2, lines 60-68, delete the extire text.

Column 3, lines 1-15, delete the entire text.

Column 3, line 68, insert after the word "flow" and before the word "62" the following text:

--directors 50, 52 such as exemplified by flat ramp surfaces 68, 70, respectively.

Flow directors 50, 52 are preferably oppositely disposed, i.e., ramp surfaces 68 and 70 are rotated 180° from each other on opposite sides of common axis 28 to render sample site 60 bidirectional. With sample site 60, it is believed that fluid 20 will flow into cavity 14 along a ramp surface (such as ramp surface 68 or 70 depending upon the direction of flow) so as to be diverted from common axis 28 and either towards Faultless 5218 pure gum latex seal 22 at the top end of cavity 14 or towards bottom end 72 of cavity 14. The continued flow of fluid 20 into one port is believed to cause fluid 20 to move towards the opposite end (top to bottom or bottom to top) of cavity 14 and swirl about until it exits the opposite port thereby flushing out the other fluid 42 (see FIG. 1) which might otherwise remain in cavity 14.

UNITED STATES PATENT AND TRADEMARK OFFICE
CERTIFICATE OF CORRECTION

PATENT NO. : 5,221,271

DATED : June 22, 1993

INVENTOR(S) : Warren B. Nicholson et al

It is certified that error appears in the above-indentified patent and that said Letters Patent is hereby corrected as shown below:

Column 3, line 68: con't

Sample site 60 is designed for use with adult patients (not shown). To this end, in polycarbonate housing 12, the diameter of cavity 14 between ports 24, 26 is about 0.220 inch with a hemispherical bottom end surface 72 having a radius of about 0.118 inch; the diameter of the cylindrical portion of ports 24, 26 is about 0.123 inch with a slight draft, and the cross-section changes from circular with a diameter of about 0.109 inch at base--.

Signed and Sealed this

Twenty-first Day of June, 1994

Attest:

BRUCE LEHMAN

*Attesting Officer*     *Commissioner of Patents and Trademarks*